United States Patent
Perkins et al.

(10) Patent No.: US 10,548,529 B2
(45) Date of Patent: Feb. 4, 2020

(54) RETENTION SYSTEM FOR ELECTRONIC DEVICES

(71) Applicant: Apple Inc., Cupertino, CA (US)

(72) Inventors: Ryan C. Perkins, San Francisco, CA (US); Trevor J. Ness, Santa Cruz, CA (US); Tobias J. Harrison-Noonan, San Francisco, CA (US); William H. Greenbaum, Mountain View, CA (US); Tyler S. Bushnell, Mountain View, CA (US); Guocheng Shao, Campbell, CA (US); Guanyi Gao, Cupertino, CA (US); Christopher M. Werner, San Jose, CA (US); Phil M. Hobson, Menlo Park, CA (US)

(73) Assignee: Apple Inc., Cupertino, CA (US)

( * ) Notice: Subject to any disclaimer, the term of this patent is extended or adjusted under 35 U.S.C. 154(b) by 0 days.

(21) Appl. No.: 16/367,020

(22) Filed: Mar. 27, 2019

(65) Prior Publication Data

US 2019/0282163 A1    Sep. 19, 2019

Related U.S. Application Data

(63) Continuation of application No. 15/700,808, filed on Sep. 11, 2017, now Pat. No. 10,285,643.

(51) Int. Cl.
*G06F 1/16* (2006.01)
*H05K 5/00* (2006.01)
(Continued)

(52) U.S. Cl.
CPC ............ *A61B 5/681* (2013.01); *A61B 5/0059* (2013.01); *G04B 37/00* (2013.01); *G04B 37/005* (2013.01); *G04B 37/08* (2013.01)

(58) Field of Classification Search
CPC .......... G06F 1/163; G06F 1/16; G06F 1/1613; G06F 1/1626; A61B 5/681; A61B 5/0059
(Continued)

(56) References Cited

U.S. PATENT DOCUMENTS

| 4,903,253 A | 2/1990 | Nikles |
| 4,958,279 A * | 9/1990 | Proellochs .......... G04B 37/1433 224/179 |

(Continued)

FOREIGN PATENT DOCUMENTS

| CN | 10656044 | 2/2017 |
| EP | 1434114 | 6/2004 |

(Continued)

OTHER PUBLICATIONS

International Search Report and Written Opinion from PCT/US2018/047380, dated Nov. 29, 2018, 12 pages.
(Continued)

*Primary Examiner* — Anthony M Haughton
(74) *Attorney, Agent, or Firm* — Morgan, Lewis & Bockius LLP (57) ABSTRACT

An assembly for a consumer product, such as a wristwatch or other wearable electronic device, can securely retain a cover member against a housing of the product. A retaining member from within the housing can engage and secure the cover member to provide a fluid barrier. The cover member can include a window or other components of a sensor device. The parts can be easily disassembled without causing permanent damage.

20 Claims, 9 Drawing Sheets

(51) Int. Cl.
*H05K 7/00* (2006.01)
*A61B 5/00* (2006.01)
*G04B 37/08* (2006.01)
*G04B 37/00* (2006.01)

(58) Field of Classification Search
USPC .................................... 361/679.01–679.03
See application file for complete search history.

(56) References Cited

U.S. PATENT DOCUMENTS

| | | | |
|---|---|---|---|
| 6,971,789 B2 * | 12/2005 | Nakamura | G04B 37/04 |
| | | | 368/281 |
| 7,126,483 B2 | 10/2006 | Zarouri | |
| 9,721,452 B2 | 8/2017 | Felch | |
| 2008/0049560 A1 | 2/2008 | Clarkson | |
| 2011/0007468 A1 | 1/2011 | Burton et al. | |
| 2013/0235546 A1 * | 9/2013 | Sedillo | H05K 7/02 |
| | | | 361/809 |
| 2013/0261405 A1 | 10/2013 | Lee | |
| 2013/0272103 A1 | 10/2013 | Mong | |
| 2016/0058375 A1 | 3/2016 | Rothkopf | |
| 2016/0069371 A1 | 3/2016 | Chen | |
| 2016/0128209 A1 * | 5/2016 | Yoon | G01R 33/07 |
| | | | 361/679.01 |
| 2016/0313700 A1 | 10/2016 | Fraser | |

FOREIGN PATENT DOCUMENTS

| | | |
|---|---|---|
| TW | 201626635 | 7/2016 |
| TW | I632447 | 8/2018 |

OTHER PUBLICATIONS

Taiwanese Office Action from Taiwanese Application No. 107129272, dated May 21, 2019, 7 pages, including English language translation.

* cited by examiner

RETENTION SYSTEM FOR ELECTRONIC DEVICES

CROSS-REFERENCE TO RELATED APPLICATION

This application is a continuation of U.S. patent application Ser. No. 15/700,808, filed Sep. 11, 2017, the disclosure of which is hereby incorporated herein by reference in its entirety.

TECHNICAL FIELD

The present description relates generally to assembly systems for devices, and, more particularly, to retention systems for wearable electronic devices.

BACKGROUND

Portable electronic devices have become increasingly popular, and the features and functionality provided by portable electronic devices continue to expand to meet the needs and expectations of many consumers. As such devices become more useful, users tend to keep the devices with them throughout the day. Some devices, such as wristwatches, are frequently carried or worn by users and exposed to a variety of conditions. For example, users may wear a watch while exercising, swimming, and bathing. As such, many watches are designed with waterproof features to protect the internal components from an external environment.

In some devices, an adhesive is utilized to secure the parts and provide a waterproof connection. The adhesive must be strong, reliable, and applied over a relatively wide extent. However, this can be unsightly because the applied adhesive may be externally visible. Furthermore, any adhesive forced out during assembly must be removed. Additionally, when a broken or cracked part is to be replaced, it often must be replaced together with any other part to which it was adhered.

BRIEF DESCRIPTION OF THE DRAWINGS

Certain features of the subject technology are set forth in the appended claims. However, for purpose of explanation, several embodiments of the subject technology are set forth in the following figures.

DETAILED DESCRIPTION

The detailed description set forth below is intended as a description of various configurations of the subject technology and is not intended to represent the only configurations in which the subject technology may be practiced. The appended drawings are incorporated herein and constitute a part of the detailed description. The detailed description includes specific details for the purpose of providing a thorough understanding of the subject technology. However, it will be clear and apparent to those skilled in the art that the subject technology is not limited to the specific details set forth herein and may be practiced without these specific details. In some instances, well-known structures and components are shown in block diagram form in order to avoid obscuring the concepts of the subject technology.

Consumer products, such as wearable electronic devices, can include various parts that are assembled together. The assembly can include a housing to contain internal components and a cover member to cover the internal components from an external environment. With some products, such as electronic devices, it can be beneficial to isolate the internal components from fluid or foreign objects. For example, it can be desirable to provide a waterproof enclosure to an electronic device so the device can safely be worn during exposure to water.

However, to provide waterproof features to some devices, the assembled parts must be sufficiently rigid where joined together to withstand the forces and strain placed thereon. Such requirements limit the selections of available material and construction and create additional expense. Some devices require adhesives to join the parts together, which can cause the parts to be unable to be separated without causing permanent damage. It can be desirable to provide a waterproof seal that does not place excessive forces on the assembled parts and can be capable of disassembly without permanently damaging the parts.

Embodiments of the present disclosure provide an assembly for a consumer product that provides a fluid barrier between the internal components and an external environment. Embodiments of the present disclosure also provide a fluid barrier even between parts that are not rigid, thereby reducing the cost and complexity of manufacture. Embodiments of the present disclosure provide a mechanism that facilitates alignment of the parts without complex or expensive machinery. Embodiments of the present disclosure also provide a mechanism for disassembling the parts without causing permanent damage.

In some embodiments, the consumer product is a portable and wearable consumer product. A wearable consumer product is one that can be worn by or otherwise secured to a user. For example, the consumer product can be a wearable electronic device including, but not limited to, a wearable computer, a wearable watch, a wearable communication device, a wearable media player, a wearable health monitoring device, and the like. In some embodiments, the consumer product includes one or more biosensors. The biosensors can include optical and/or electronic biometric sensors that can be used to compute one or more health metrics. Optical components of the biosensor, such as lenses, can be integrated into a cover member that is secured to a housing of a consumer product with a fluid barrier.

These and other embodiments are discussed below with reference to FIGS. 1-11. However, those skilled in the art will readily appreciate that the detailed description given herein with respect to these figures is for explanatory purposes only and should not be construed as limiting.

Figure 1:
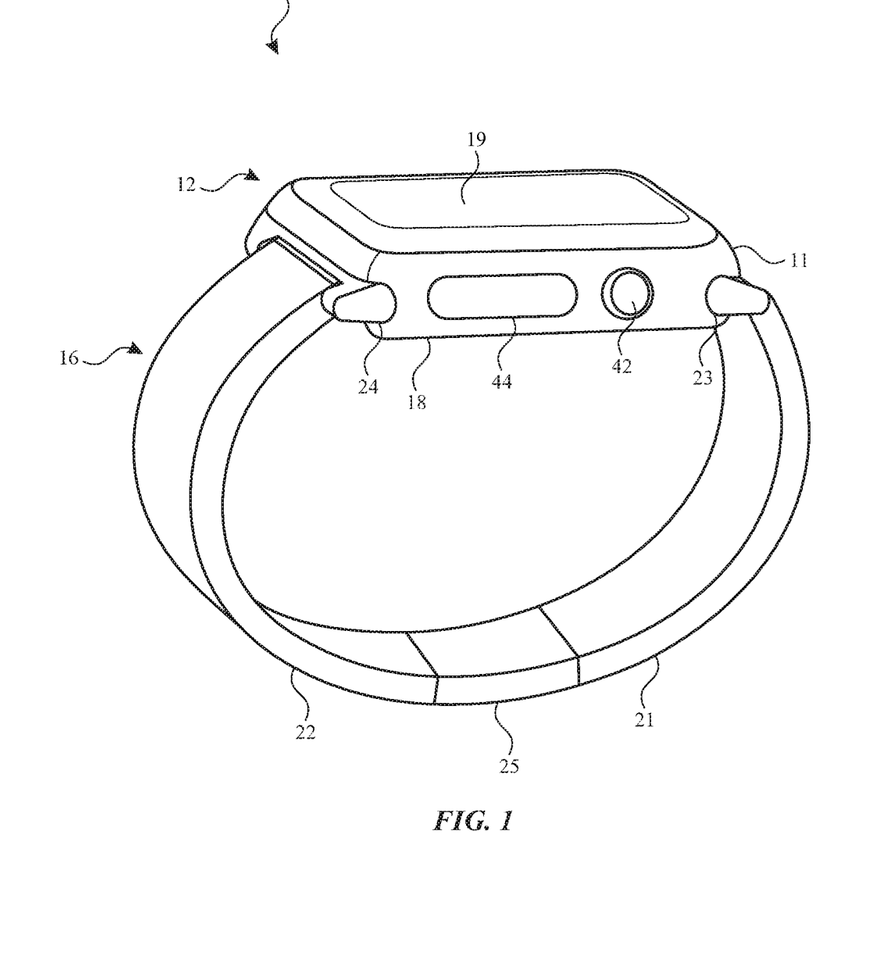
FIG. 1 shows a perspective view of an exemplary watch.

Referring to FIG. 1, an exemplary consumer product can be a wearable electronic device 10, such as a wristwatch. While FIG. 1 illustrates device 10 as a watch, it will be recognized that features described herein with respect to the device 10 can be applied to a variety of other devices, such as portable computing devices, cell phones, smart phones, tablet computers, laptop computers, cameras, timekeeping devices, computerized glasses, and other wearable devices navigation devices, displays, sports devices, accessory devices, health-monitoring devices, medical devices, wristbands, bracelets, jewelry, and/or the like.

As shown in FIG. 1, the device 10 includes a device body 12 that can be attached to a user's wrist using a band 16. In the present example, the band 16 include a first band strap 21 attached to a first receiving feature 23 and a second band strap 22 attached to a second receiving feature 24. In some embodiments, the first and second band straps 21, 22 include a lug feature that is configured to attach to the first and second receiving features 23, 24, respectively. As shown in FIG. 1, the free ends of the band straps 21, 22 are connected with a clasp 25.

One of the components included in the device body 12 can be one or more I/O systems. For example, the display 19 can be configured to output various information about the device body 12. The display 19 can also be configured to receive input. The device body 12 can also have other input and output mechanisms. For example, the device body 12 can include or interface with one or more buttons, crowns, keys, dials, trackpads, microphones and the like for receiving input from a user. As shown in FIG. 1, the device body 12 can include a button 44 and a crown 42.

The device body 12 can include a housing 11 that supports the display 19. The housing 11 serves to surround a peripheral region of the device body 12 as well as support the internal components of the device body 12 in their assembled position. For example, the housing 11 encloses and supports various internal components (including for example integrated circuit chips, processors, memory devices and other circuitry) to provide computing and functional operations for the device body 12. Opposite the display 19, the housing 11 can include an outer surface 18 on a rear-facing side of the housing 11.

Figure 2:
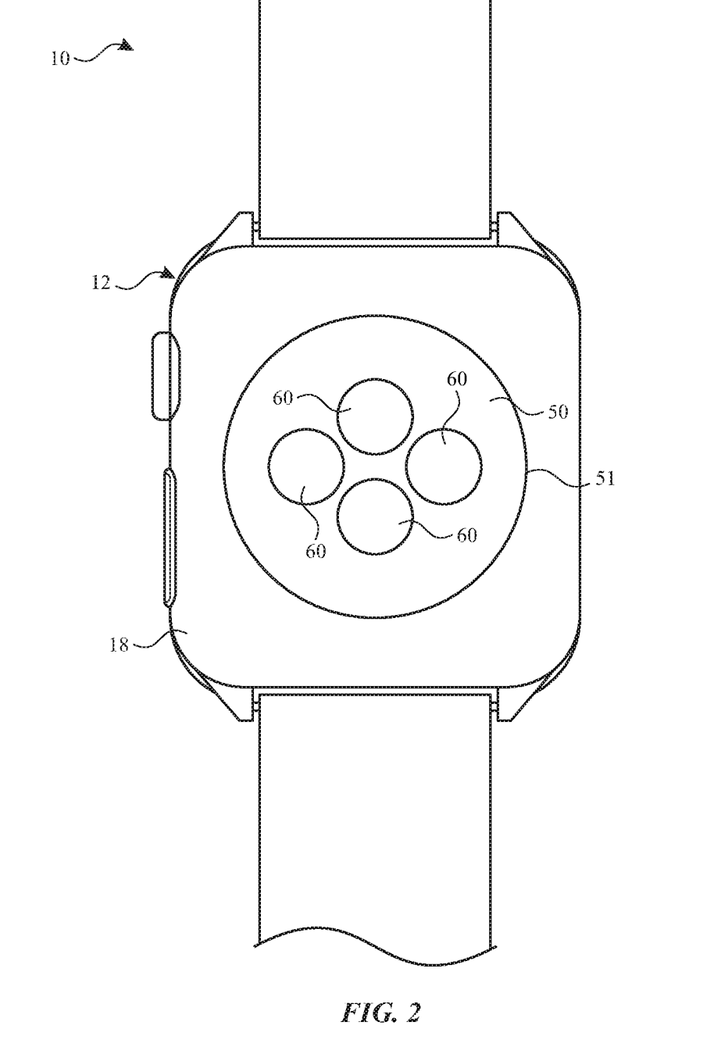
FIG. 2 shows a rear view of an exemplary watch housing of the watch of FIG. 1.

Referring to FIG. 2, a biosensor module 51 of the device body 12 can be positioned in an opening formed in the housing 11 and on the outer surface 18 of the housing 11. The biosensor module 51 can include a cover member 50 that facilitates attachment of the biosensor module 51 to the housing 11. The cover member 50 can include features or elements that facilitate a watertight seal between the biosensor module 51 and the housing 11, as described further herein.

The biosensor module 51 can include or support one or more sensor devices 60 configured to detect and measure a physiological condition or property of the user. Various sensor devices 60 for measuring and collecting data that can be used to calculate a health metric or other health-related information. The device body 12 of the device 10 can include one or more light sources and one or more light detectors that are configured to function as an optical sensor or sensors. The sensor devices 60 can be implemented as a pairing of one or more light sources and detectors. The detector is configured to collect light and convert the collected light into an electrical sensor signal that corresponds to the amount of light incident on a surface of the detector. The detector can be a photodetector, such as a photodiode, phototube, photosensor, or other light-sensitive device. In some cases, the sensor devices 60 can operate as a photoplethysmography ("PPG") sensor or sensors. In some instances, a PPG sensor is configured to measure light and produce a sensor signal that can be used to estimate changes in the volume of a part of a user's body. In general, as light from the one or more light sources passes through the user's skin and into the underlying tissue, some light is reflected, some is scattered, and some light is absorbed, depending on what the light encounters. The light that is received by a sensor device 60 can be used to generate a sensor signal, which can be used to estimate or compute a health metric or other physiological phenomena. While FIG. 2 depicts one example embodiment, the number of sensor devices 60 (e.g., light sources and/or detectors) can vary in different embodiments. For example, another embodiment can use more than one detector. Another embodiment can also use fewer or more light sources than are depicted in the example of FIG. 2.

Figure 3:
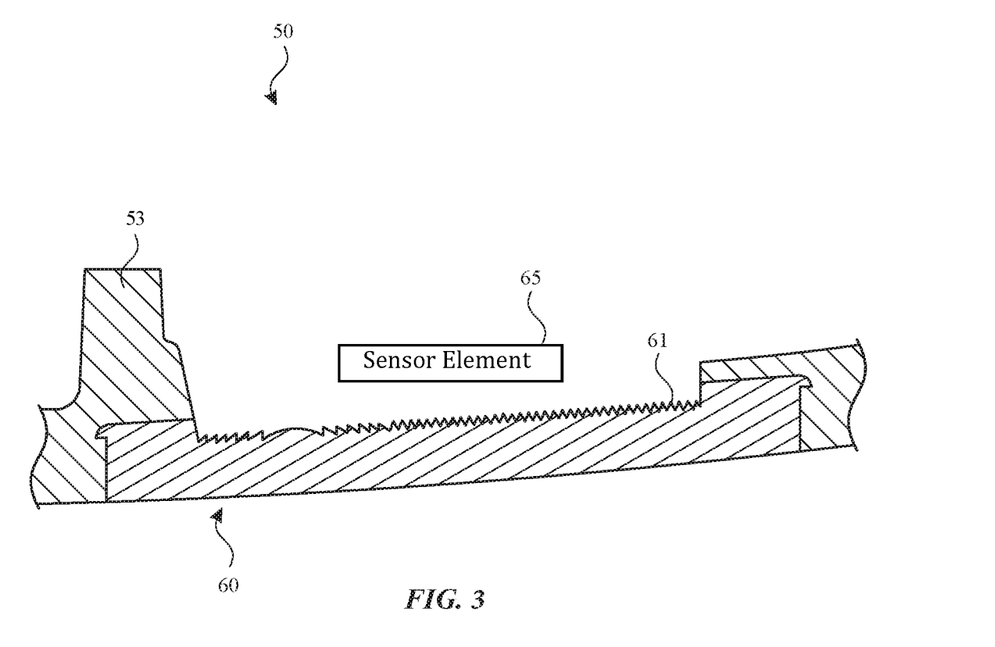
FIG. 3 shows a sectional view of an exemplary watch housing having a lens.

Referring to FIG. 3, the cover member 50 can include a cover body 53 in which the sensor devices 60 are positioned. Each of the sensor devices 60 can include a window 61 that transmits light to or from a sensor element 65 of the sensor device 60. The sensor element 65 of the sensor device 60 can include a light source and/or a detector. The sensor element 65 can be aligned with and positioned on a side of the window 61 that is facing an interior of the device body 12 when the cover member 50 is connected to the device body 12. The window 61 can have properties that enhance the function of the sensor device 60 as well as providing an aesthetically pleasing appearance. The window 61 can be joined with the cover body 53 of the cover member 50. For example, both the cover body 53 and a window 61 can be molded from plastic material(s). The shape and features of the cover body 53 and the window 61 can be formed by a mold when the material is injected therein. The cover body 53 and the window 61 can be formed in separate stages of a molding process (e.g., by two-shot injection molding).

While the biosensor module 51 of FIG. 2 is illustrated with light-based sensing capabilities, the biosensor module 51 can also include one or more electrodes to measure electrical properties of the user's body. For example, multiple electrodes can be disposed on cover member 50 and configured to make contact with the skin of the user's wrist when the device is being worn. Other types of biosensor capabilities are contemplated for implementation into the biosensor module 51.

As shown in FIG. 3, the window 61 can be formed to include a shape or pattern that defines a lens, such as a Fresnel lens. Features of a Fresnel lens (e.g., concentric ridges) can be formed on an inner and/or outer surface of the window 61. As a lens, the window 61 can refract light to direct the light to or from the sensor element 65. A pattern of the window 61 can also be aesthetically pleasing and obscure a view of the sensor element 65. The window 61 can be a unibody structure, rather than an assembly of parts. As used herein, a unibody structure is one that is integrally formed of a single piece. For example, the window 61 can be a monolithic structure. By providing a unibody window 61, the window 61 is formed to its preferred size and shape in one step, thereby reducing complexity and cost of construction. The unibody window 61 can extend from an interior of the housing to an exterior of the housing.

While FIGS. 2 and 3 illustrates windows 61 (e.g. lenses) of a device 10 (e.g., a watch), it will be recognized that features described herein with respect to retention of the cover member 50 can be applied to a variety of other components. For example, the retention mechanisms described herein with respect to the cover member 50 can be applied to any part that is desirably retained to a housing. For example, the retention mechanisms described herein can be applied to a lens of a camera, a display of an electronic device, a user input module (e.g., button) of a device, and/or the like.

Figure 4:
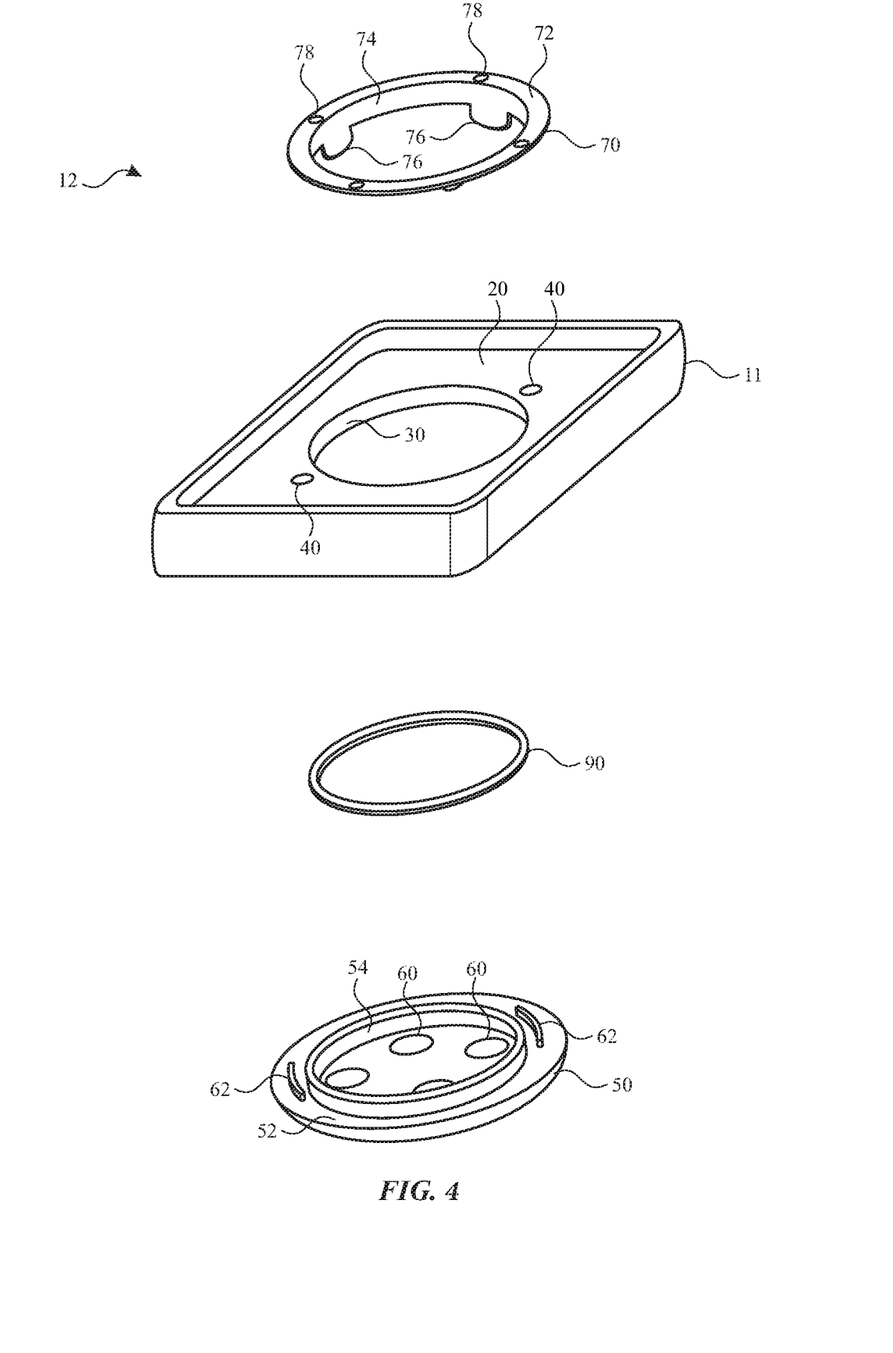
FIG. 4 shows an exploded perspective view of an exemplary watch housing.
Figure 5:
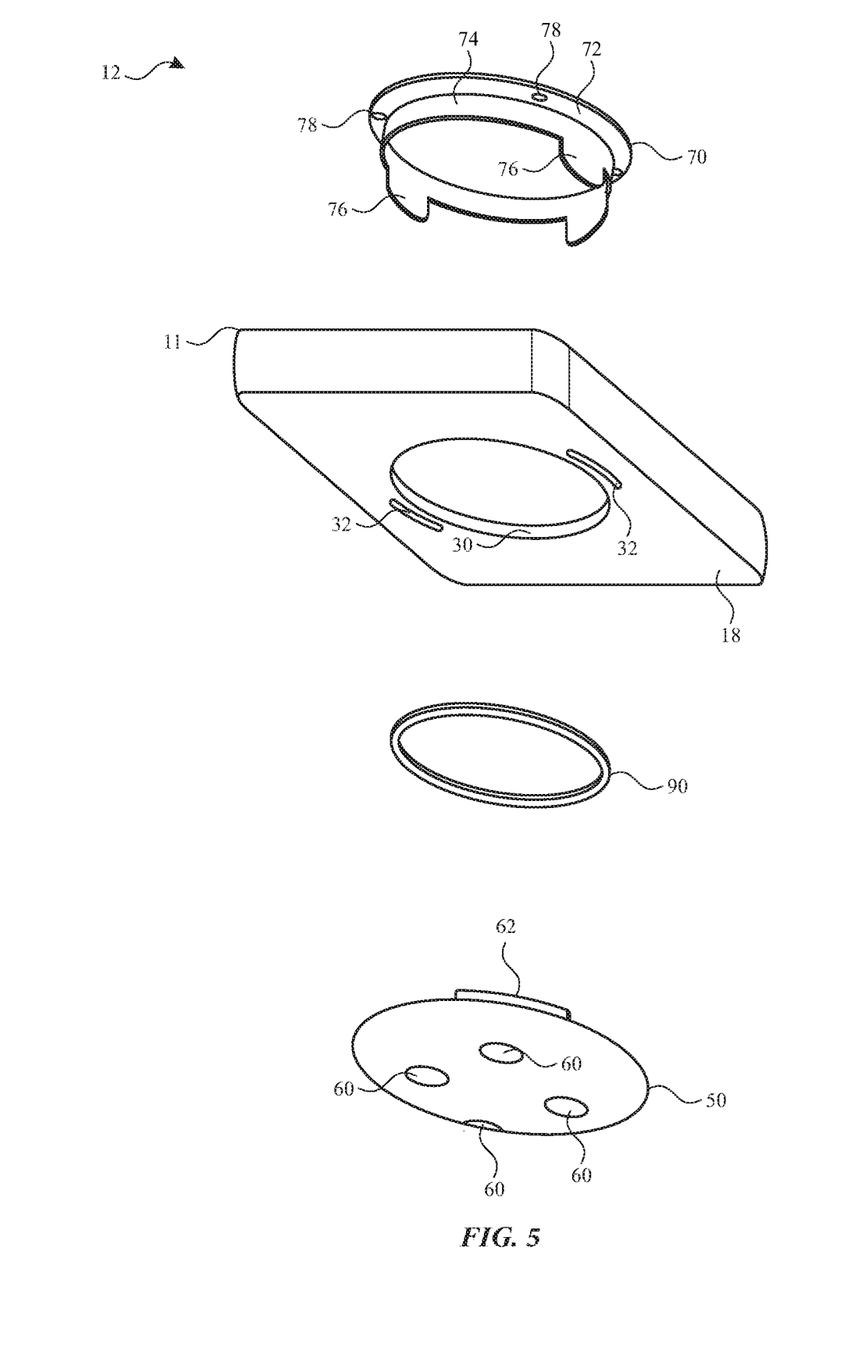
FIG. 5 shows another exploded perspective view of the watch housing of FIG. 4.

Referring to FIGS. 4 and 5, the cover member 50 can be secured to the housing 11 by a retention member 70. The housing 11 can include an opening 30 that extends through a side of the housing 11. For example, the opening 30 can extend from an outer surface 18 to an inner surface 20 of the housing 11. While the opening 30 and items positioned therein are illustrated as being round, other shapes are contemplated, including oval and polygonal. On the inner surface 20 of the housing 11, one or more depressions 40 can be provided for engagement by the retention member 70, as described further herein. On the outer surface 18 of the housing 11, one or more alignment channels 32 can be provided for engagement by the cover member 50, as described further herein.

The components (e.g., sensor devices 60) of a biosensor module can be integrated into the cover member 50, which is separate from and attached to the housing 11 of the device 10. For example, the cover member 50 can be positioned at least partially within the opening 30 of the housing 11 and at least partially against the outer surface 18 of the housing 11. The outer surface 18 of the housing 11 can have a flat, convex, or concave shape, and the cover member 50 can have an engagement surface 52 that complements and engages the outer surface 18. The cover member 50 can include an extension section 54 that extends at least partially into or through the openings 30 of the housing 11. While the extension section 54 and other portions of the cover member 50 are illustrated as being round, other shapes are contemplated, including oval and polygonal. The extension section 54 can have a shape and size that is complementary to a shape and size of the opening 30.

Along the engagement surface 52, the cover member 50 can provide one or more alignment elements 62 for engaging the one or more alignment channels 32 of the housing 11. The alignment element 62 can have a size and/or shape that is complementary to the size and/or shape of the alignment channels 32. For example, the alignment channels 32 extend only partially circumferentially. By positioning the alignment elements 62 of the cover member 50 within the alignment channels 32 of the housing 11, the cover member 50 can be maintained at a particular rotational orientation with respect to the housing 11. The rotational orientation can be a preferred rotational orientation for assembly and operation of the device body 12. Accordingly, the device body 12 provides ease of alignment during assembly and maintenance of the alignment thereafter. While the alignment elements 62 are shown on the cover member 50 and the alignment channels 32 are shown on the housing 11, it will be understood that the components can be arranged such that alignment elements are provided on the housing 11 and alignment channels are provided on the cover member 50. Additionally or alternatively, the cover member 50 and the housing 11 can each include an alignment element and an alignment channel.

A seal member 90 can be provided between the cover member 50 and the housing 11. The seal member 90 can be a compliant ring that extend circumferentially about and/or against a portion of the cover member 50, such as the extension section 54. For example, the seal member 90 can be of an elastic material the serves as a mechanical gasket when placed between the cover member 50 and the housing 11. For example, the seal member can include nitrile, silicone, another polymer, or combinations thereof.

The retention member 70 can be positioned at least partially within a portion of the housing 11, for example against an inner surface 20 of the housing 11. The retention member 70 can be positioned at least partially within the opening 30 of the housing 11 and/or a portion of the cover member 50 for engagement therewith. The cover member 50 can include a support section 74 that extends axially through the opening 30. The cover member 50 can further include a flange 72 that extends radially outwardly from the support section 74 for contacting the inner surface 20 of the housing 11. The cover member 50 can further include one or more engagement elements 76 that extend radially outwardly from the support section 74 to engage the cover member 50, as described further herein. The retention member 70 can include, for example along the flange 72, one or more holes 78 for engagement by user to apply a torque to the retention member 70. While the support section 74 and other portions of the retention member 70 are illustrated as being round, other shapes are contemplated, including oval and polygonal. The support section 74 can have a shape and size that is complementary to a shape and size of the opening 30.

Figure 6:
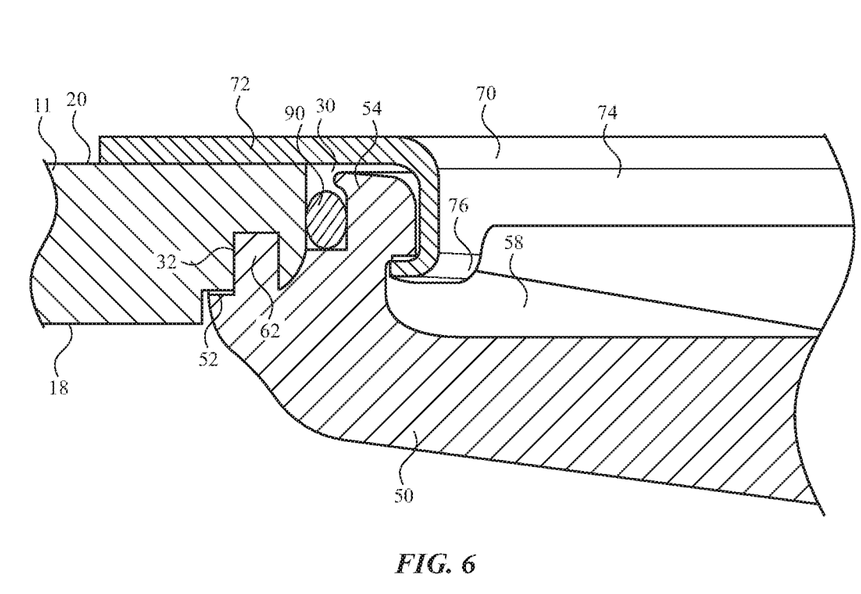
FIG. 6 shows a sectional view of an exemplary watch housing.

Referring to FIG. 6, the cover member 50 can be secured to the housing 11 by the retention member 70. The cover member 50 can be positioned over the opening 30, with the engagement surface 52 of the cover member 50 against the outer surface 18 of the housing 11. Furthermore, the alignment element 62 of the cover member 50 can be positioned within alignment channel 32 of the housing 11. The seal member 90 can be positioned between the cover member 50 and housing 11. While the seal member 90 is illustrated as being positioned radially between a portion of the cover member 50 and a portion of the housing 11, it will be understood that the seal member 90 can also be positioned elsewhere, such as axially between a portion of the cover member 50 and a portion of the housing 11. The seal member 90 forms a fluid barrier between the housing 11 and the cover member 50. For example, the seal member 90 forms a watertight, water-resistant, and/or airtight seal. Accordingly, components within an internal space of the housing 11 can be protected from elements of the external environment.

The cover member 50 and the seal member 90 can be secured to the housing 11 by the retention member 70. As shown in FIG. 6, the flange 72 of the retention member 70 extends radially outwardly from the support section 74 to the inner surface 20 of the housing 11. The support section 74 extends into at least a portion of the cover member 50. The engagement element 76 extends radially outwardly from the support section 74 to the cover member 50. While the engagement element 76 is shown extending radially outwardly to an inner surface of the cover member 50, it will be understood that other arrangements are contemplated, such as an engagement element of the retention member 70 that extends radially inwardly to an outer surface of the cover member 50.

As further shown in FIG. 6, the cover member 50 can include one or more engagement channels 58, for example on a radially inner surface of the extension section 54. The engagement channels 58 can each have a tapered height, and the retention member 70 comprises engagement element 76s extending radially outwardly to engage the engagement channels 58. The engagement elements 76 of the cover member 50 can extend into corresponding engagement channels 58 to allow the cover member 50 to be threaded onto the retention member 70. As the retention member 70 rotates with respect to the cover member 50, each engagement element 76 is moved to a different portion of the corresponding engagement channels 58, for example a portion having a different height. Accordingly, rotation of the retention member 70 relative to the cover member 50 adjusts a distance between the cover member 50 and the housing 11. When the cover member 50 is brought into contact with the outer surface 18 of the housing 11, rotation of the retention member 70 can cease. As such, the retention member 70 is rotatable relative to the housing 11 and the cover member 50 to secure the cover member 50 against the housing 11.

Figure 7:
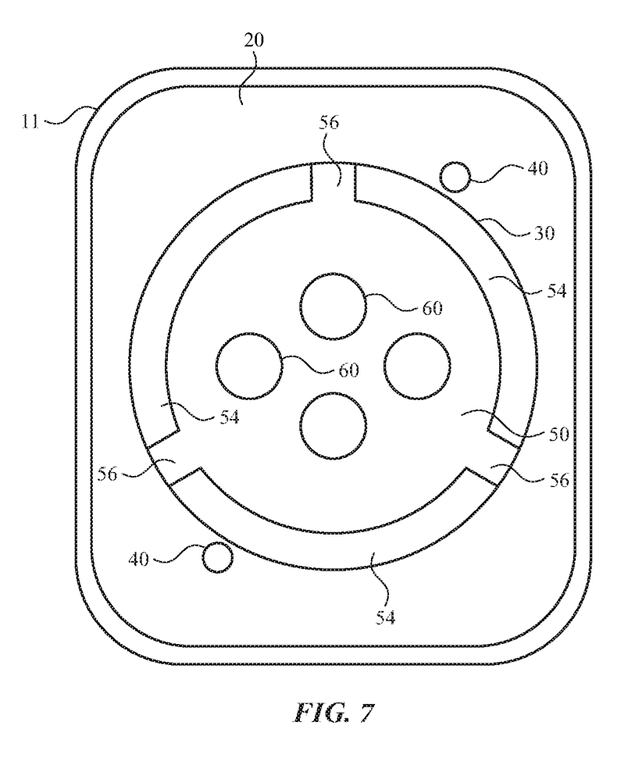
FIG. 7 shows a front view of an exemplary watch housing in a first stage of assembly.
Figure 8:
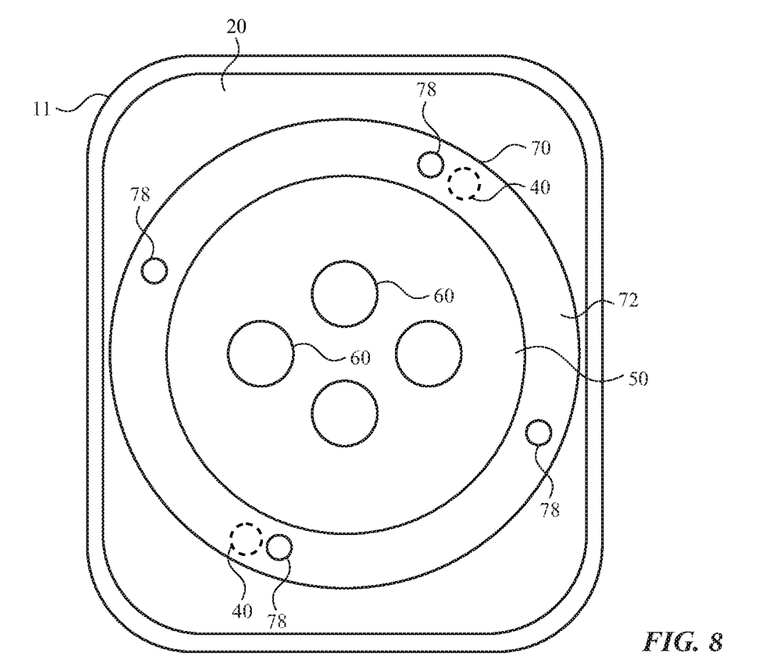
FIG. 8 shows a front view of the watch housing of FIG. 7 in a second stage of assembly.
Figure 9:
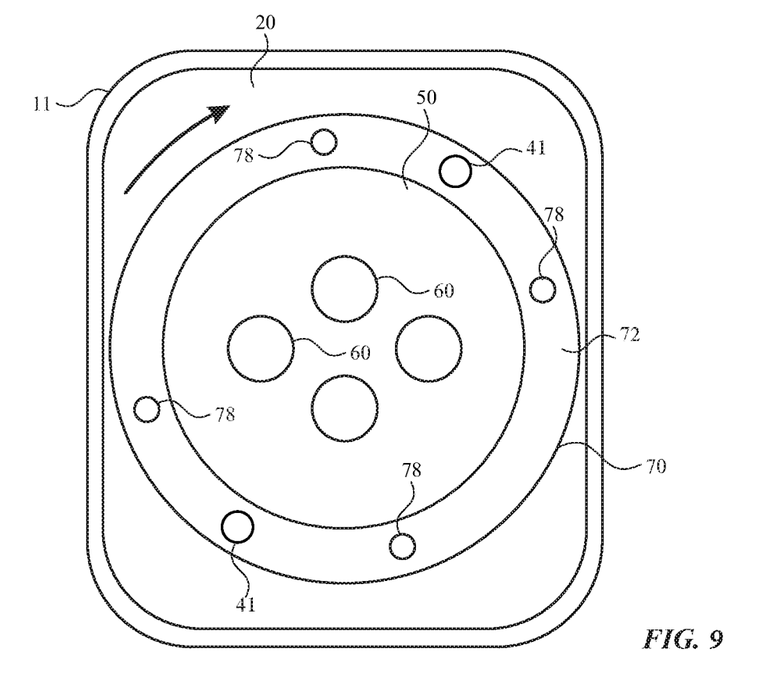
FIG. 9 shows a front view of the watch housing of FIG. 7 in a third stage of assembly.

Referring to FIGS. 7-9, a retention member can be engaged onto a cover member to secure the cover member against the housing. As shown in FIG. 7, the cover member 50 can be positioned at or near the housing 11. For example, the extension section 54 of the cover member 50 can extend at least partially into or through the opening 30 of the housing 11. The cover member 50 can be positioned so that the sensor devices 60 have a preferred location and orientation. The extension section 54 can include one or more gaps 56 that provide access to engagement channels of the cover member 50. The gaps 56 can extend axially along the extension section 54 so that a portion of a retention member can be inserted into the gaps 56 to enter the engagement channels.

As shown in FIG. 8, the retention member 70 can be positioned at or near the inner surface 20 of the housing 11. The engagement elements (not shown) can be inserted into the gaps 56 of the extension section 54 (see FIG. 7). As further shown in FIG. 8, the retention member 70 can include, for example along the flange 72, one or more holes 78. The holes 78 can provide an engagement location for a tool operated by a user or machine. The flange 72 can rotate over the inner surface 20 and depressions 40 of the housing 11.

As shown in FIG. 9, the retention member 70 can be rotated relative to housing 11 and the cover member 50. As a user applies a torque to the retention member 70 (e.g., at the holes 78), the engagement elements (not shown) can engage a tapered portion of an engagement channel of the cover member 50 (see FIG. 6). The retention member 70 can be rotated until the retention member 70 and/or the cover member 50 reaches a preferred location. For example, the retention member 70 can be rotated at least until the cover member 50 contacts an outer surface of the housing 11. By further example, the retention member 70 can be rotated until a torque that would be required for further rotation exceeds a threshold. The threshold can be predetermined, and the applied torque can be sensed during rotation, so that rotation can cease when the applied torque reaches or exceeds the threshold. For example, the threshold can be about 1 N·m, 2 N·m, 3 N·m, or greater than 3 N·m. Additionally or alternatively, the threshold can be less than about 1 N·m.

As further shown in FIG. 9, the retention member 70 can be removably secured to the housing 11 to retain the cover member 50. For example, when the retention member 70 is installed, at least a portion (e.g., flange 72) of the retention member 70 can be aligned with the depression 40 of the housing 11. Each portion 41 of the flange 72 that overlies a depression 40 can be deformed (e.g., plastically deformed) into the depression 40. When the portions 41 have been deformed, the torque required to further rotate the retention member 70 can be greater than before the deformation has occurred. For example, further rotation can require that the deformed portions 41 of the flange 72 move out of the depressions 40 to allow rotation. As such, the retention member 70 can be secured to the housing 11 such that removal requires a torque greater than the torque applied for installation (e.g., the threshold torque). For example, the torque required for removal after deformation can be about 4 N·m, 5 N·m, 6 N·m, 7 N·m, 8 N·m, 9 N·m, 10 N·m, or greater than 10 N·m.

Additionally or alternatively, the retention member 70 and/or the cover member 50 can be secured with other mechanisms. For example, an adhesive can be applied between the retention member 70 and the housing 11, between the cover member 50 and the housing 11, and/or between the retention member 70 and the cover member 50. However, it will be recognized that adhesives are not required to secure the cover member 50 and the retention member 70.

Figure 10:
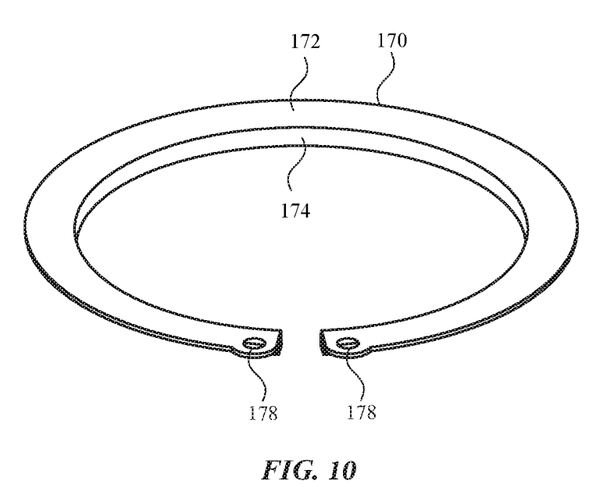
FIG. 10 shows a perspective view of an exemplary retention member.
Figure 11:
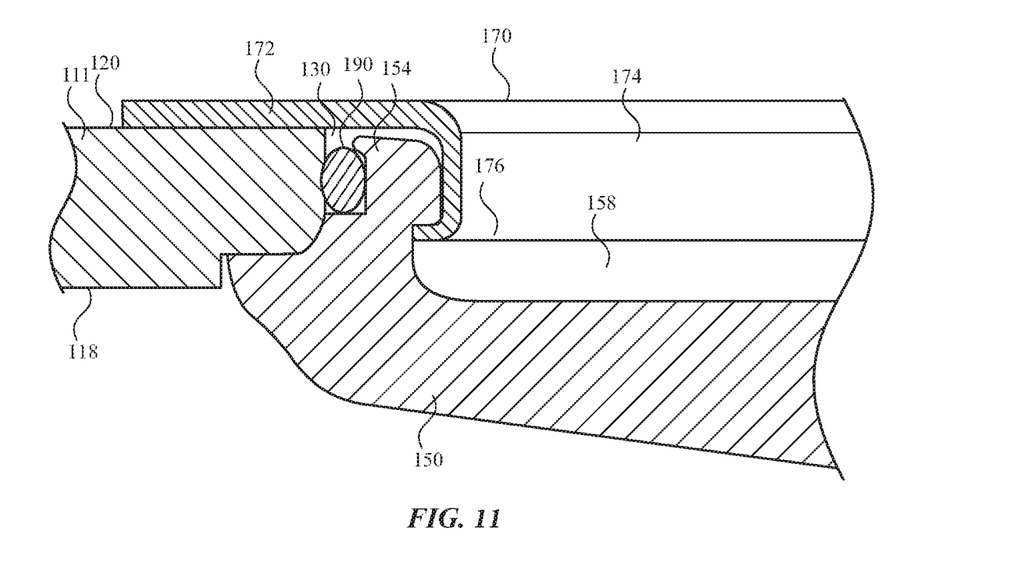
FIG. 11 shows a sectional view of an exemplary watch housing.

Referring to FIGS. 10 and 11, a retention member can be engaged onto a cover member to secure the cover member against the housing without requiring rotation. As shown in FIG. 10, a retention member 170 can have a shape and construction that allows adjustment to engage the cover member. For example, the retention member 170 can be circumferentially discontinuous, so that the retention member 170 can be elastically compressed. Compression of the retention member 170 causes a dimension (e.g., diameter) of the retention member 170 to be decreased temporarily to facilitate insertion of the retention member 170 into the cover member. As further shown in FIG. 10, the retention member 170 can include, for example along a flange 172, one or more holes 178 for engagement by user to apply a force to the retention member 170. For example, a user can engage the holes 178 and move them closer to each other to decrease a dimension of the retention member 170.

As shown in FIG. 11, the cover member 150 can include a support section 174 for extending axially through an opening of the cover member. The flange 172 of the retention member 170 extends radially outwardly from the support section 174 for contacting an inner surface of the housing. While support section 174 and other portions of the retention member 170 are illustrated as being round, other shapes are contemplated, including oval and polygonal. The extension section 154 can have a shape and size that is complementary to a shape and size of an opening of the housing.

As further shown in FIG. 11, the retention member 170 can be positioned at least partially within a portion of the housing 111, for example against an inner surface 120 of the housing 111. The retention member 170 can be positioned at least partially within the opening 130 of the housing 111 and/or a portion of the cover member 150 for engagement therewith. When the retention member 170 is expanded (e.g., released) within the cover member 150, an engagement element 176 of the retention member 170 extends radially outwardly from the support section 174 to the cover member 150. While the engagement element 176 is shown extending radially outwardly to an inner surface of the cover member 150, it will be understood that other arrangements are contemplated, such as an engagement element of the retention member 170 that extends radially inwardly to an outer surface of the cover member 150.

As further shown in FIG. 11, the cover member 150 can be positioned over the opening 130, with the engagement surface 152 of the cover member 150 against the outer surface 118 of the housing 111. While not shown in FIG. 11, an alignment element of the cover member 150 can be positioned within an alignment channel of the housing 111. The seal member 190 can be positioned between the cover member 150 and housing 111.

As further shown in FIG. 11, the cover member 150 can include an engagement channel 158, for example on a radially inner surface of the extension section 154. The engagement channel 158 can have a height that accommodates the engagement element 176 of the retention member 170. For example, the engagement channel 158 can extend partially or fully about a circumference of the extension section 154. The engagement channel 158 can receive the engagement element 176 when the retention member 170 is radially expanded, so that the retention member 170 secures the cover member 150 against the outer surface 118 of the housing 111.

Figure 12:
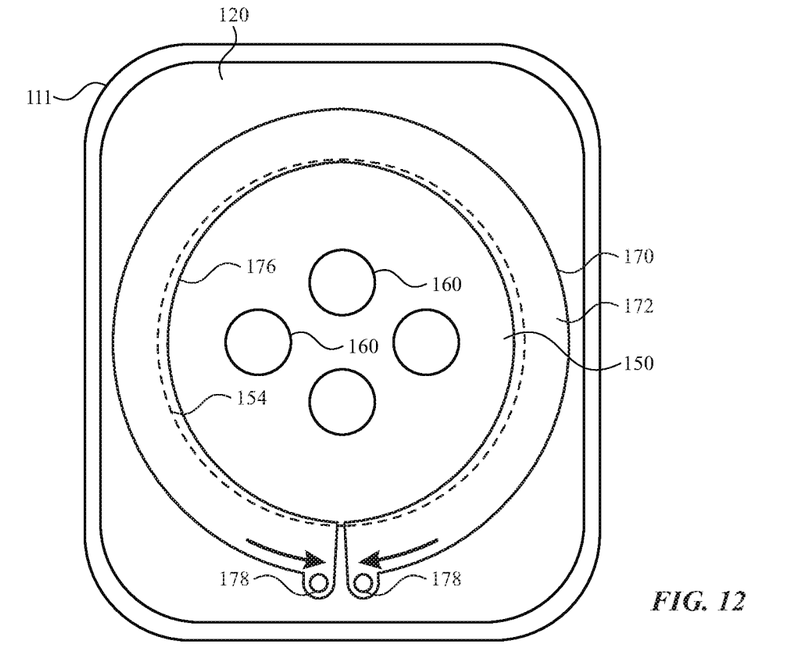
FIG. 12 shows a front view of an exemplary watch housing in a first stage of assembly.
Figure 13:
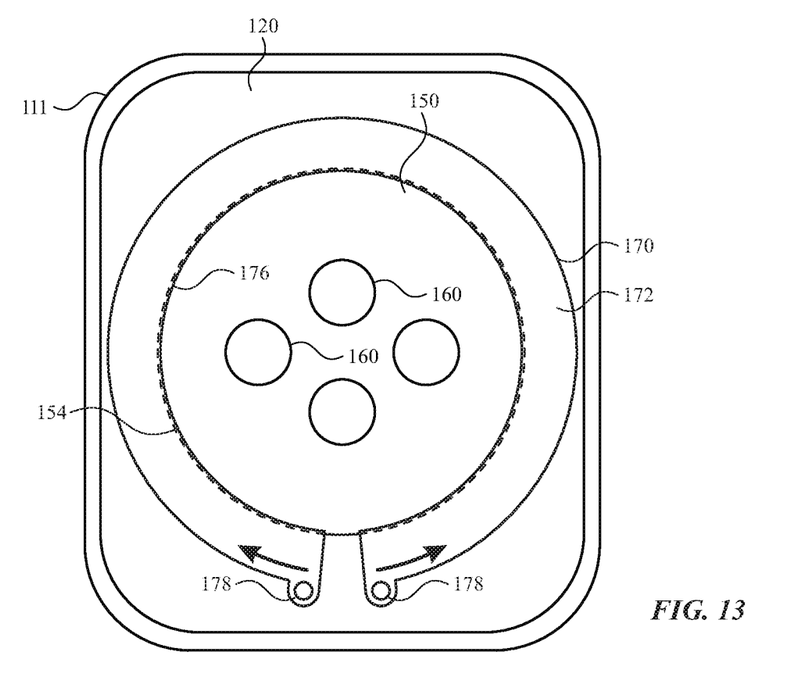
FIG. 13 shows a front view of the watch housing of FIG. 12 in a second stage of assembly.

Referring to FIGS. 12 and 13, a retention member can be engaged onto a cover member to secure the cover member against the housing. As shown in FIG. 12, the cover member 150 can be positioned at or near the housing 111. For example, the extension section 154 of the cover member 50 can extend at least partially into or through the opening of the housing 111. The cover member 150 can be positioned so that the sensor devices 160 have a preferred location and orientation. The retention member 170 can be positioned at or near the inner surface 120 of the housing 111 in a compressed configuration having a compressed outer dimension. For example, the holes 178 can be acted upon to bring portions of the retention member 170 closer together.

As shown in FIG. 13, the retention member 170 can be expanded. For example, when the holes 178 are released, the retention member 170 can expand to increase its outer dimension. The engagement elements (not shown) can engage the engagement channel of the cover member 150 (see FIG. 11), for example, adjacent to the extension section 154.

Additionally or alternatively, the retention member 170 and/or the cover member 150 can be secured with other mechanisms. For example an adhesive can be applied between the retention member 170 and the housing 111, between the cover member 150 and the housing 111, and/or between the retention member 170 and the cover member 150. However, it will be recognized that adhesives are not required to secure the cover member 150 and the retention member 170.

Accordingly, the embodiments discussed herein provide mechanisms that facilitate secure engagement of a cover member onto a housing of a device. The mechanism provides a fluid barrier between the internal components and an external environment without requiring that the cover member itself provide the fluid barrier. Accordingly, the cover member can be of a variety of materials that need not provide rigidity for self-securement. Disassembly of the cover member can be easily achieved due to the reversible securement.

A reference to an element in the singular is not intended to mean one and only one unless specifically so stated, but rather one or more. For example, "a" module may refer to one or more modules. An element proceeded by "a," "an," "the," or "said" does not, without further constraints, preclude the existence of additional same elements.

Headings and subheadings, if any, are used for convenience only and do not limit the invention. The word exemplary is used to mean serving as an example or illustration. To the extent that the term include, have, or the like is used, such term is intended to be inclusive in a manner similar to the term comprise as comprise is interpreted when employed as a transitional word in a claim. Relational terms such as first and second and the like may be used to distinguish one entity or action from another without necessarily requiring or implying any actual such relationship or order between such entities or actions.

Phrases such as an aspect, the aspect, another aspect, some aspects, one or more aspects, an implementation, the implementation, another implementation, some implementations, one or more implementations, an embodiment, the embodiment, another embodiment, some embodiments, one or more embodiments, a configuration, the configuration, another configuration, some configurations, one or more configurations, the subject technology, the disclosure, the present disclosure, other variations thereof and alike are for convenience and do not imply that a disclosure relating to such phrase(s) is essential to the subject technology or that such disclosure applies to all configurations of the subject technology. A disclosure relating to such phrase(s) may apply to all configurations, or one or more configurations. A disclosure relating to such phrase(s) may provide one or more examples. A phrase such as an aspect or some aspects may refer to one or more aspects and vice versa, and this applies similarly to other foregoing phrases.

A phrase "at least one of" preceding a series of items, with the terms "and" or "or" to separate any of the items, modifies the list as a whole, rather than each member of the list. The phrase "at least one of" does not require selection of at least one item; rather, the phrase allows a meaning that includes at least one of any one of the items, and/or at least one of any combination of the items, and/or at least one of each of the items. By way of example, each of the phrases "at least one of A, B, and C" or "at least one of A, B, or C" refers to only A, only B, or only C; any combination of A, B, and C; and/or at least one of each of A, B, and C.

It is understood that the specific order or hierarchy of steps, operations, or processes disclosed is an illustration of exemplary approaches. Unless explicitly stated otherwise, it is understood that the specific order or hierarchy of steps, operations, or processes may be performed in different order. Some of the steps, operations, or processes may be performed simultaneously. The accompanying method claims, if any, present elements of the various steps, operations or processes in a sample order, and are not meant to be limited to the specific order or hierarchy presented. These may be performed in serial, linearly, in parallel or in different order. It should be understood that the described instructions, operations, and systems can generally be integrated together in a single software/hardware product or packaged into multiple software/hardware products.

In one aspect, a term coupled or the like may refer to being directly coupled. In another aspect, a term coupled or the like may refer to being indirectly coupled.

Terms such as top, bottom, front, rear, side, horizontal, vertical, and the like refer to an arbitrary frame of reference, rather than to the ordinary gravitational frame of reference. Thus, such a term may extend upwardly, downwardly, diagonally, or horizontally in a gravitational frame of reference.

The disclosure is provided to enable any person skilled in the art to practice the various aspects described herein. In some instances, well-known structures and components are shown in block diagram form in order to avoid obscuring the concepts of the subject technology. The disclosure provides various examples of the subject technology, and the subject technology is not limited to these examples. Various modifications to these aspects will be readily apparent to those skilled in the art, and the principles described herein may be applied to other aspects.

All structural and functional equivalents to the elements of the various aspects described throughout the disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112, sixth paragraph, unless the element is expressly recited using the phrase "means for" or, in the case of a method claim, the element is recited using the phrase "step for".

The title, background, brief description of the drawings, abstract, and drawings are hereby incorporated into the disclosure and are provided as illustrative examples of the disclosure, not as restrictive descriptions. It is submitted with the understanding that they will not be used to limit the scope or meaning of the claims. In addition, in the detailed description, it can be seen that the description provides illustrative examples and the various features are grouped together in various implementations for the purpose of streamlining the disclosure. The method of disclosure is not to be interpreted as reflecting an intention that the claimed subject matter requires more features than are expressly recited in each claim. Rather, as the claims reflect, inventive subject matter lies in less than all features of a single disclosed configuration or operation. The claims are hereby incorporated into the detailed description, with each claim standing on its own as a separately claimed subject matter.

The claims are not intended to be limited to the aspects described herein, but are to be accorded the full scope consistent with the language claims and to encompass all legal equivalents. Notwithstanding, none of the claims are intended to embrace subject matter that fails to satisfy the requirements of the applicable patent law, nor should they be interpreted in such a way.

What is claimed is:

1. A wearable electronic device comprising:
   a housing comprising sidewalls for containing electronic components, an inner surface, an outer surface, and an opening;
   a cover member positioned over the opening; and
   a retention member positioned within the housing and against the inner surface, the retention member being radially expandable relative to the cover member and the housing to secure the cover member against the outer surface of the housing.

2. The wearable electronic device of claim 1, wherein the retention member comprises:
   a support section;
   a flange extending radially outwardly from the support section to the inner surface of the housing; and
   an engagement element extending radially outwardly from the support section to the cover member.

3. The wearable electronic device of claim 1, wherein the retention member is circumferentially discontinuous.

4. The wearable electronic device of claim 1, wherein the retention member is configured to transition from a compressed configuration, in which the retention member has a first outer dimension, to an expanded configuration, in which the retention member has a second outer dimension that is greater than the first outer dimension.

5. The wearable electronic device of claim 4, wherein the retention member, while in the compressed configuration, is configured to pass through a portion of the cover member and the retention member, while in the expanded configuration, is configured to engage an inner portion of the cover member.

6. The wearable electronic device of claim 1, further comprising a seal member between the housing and the cover member that forms a fluid barrier.

7. The wearable electronic device of claim 1, further comprising:
   a biosensor module comprising a light source and a light detector;
   a display configured to output information and receive input; and
   a button for receiving input.

8. A wearable electronic device comprising:
   a housing;
   a cover member engaging an outer surface of the housing such that the cover member is moveable toward the housing while being maintained in a fixed rotational orientation relative to the housing; and
   a retention member having a circumferentially discontinuous shape and being positioned at least partially within the housing and against an inner surface of the housing opposite the cover member, the retention member being expandable relative to the cover member to secure the cover member against the housing.

9. The wearable electronic device of claim 8, wherein the cover member comprises engagement channels on an inner radial surface of the cover member, and the retention member comprises engagement elements extending radially outwardly to engage the engagement channels.

10. The wearable electronic device of claim 8, wherein the retention member comprises opposing ends that are moveable with respect to each other to change an outer dimension of the retention member.

11. The wearable electronic device of claim 8, wherein the cover member is rotationally fixed with respect to the housing when the cover member is secured against the housing.

12. The wearable electronic device of claim 8, wherein the housing comprises an alignment channel on the outer surface of the housing, and the cover member comprises an alignment element within the alignment channel of the housing, wherein the alignment channel extends only partially circumferentially.

13. The wearable electronic device of claim 8, further comprising:
   a biosensor module comprising a light source and a light detector;
   a display configured to output information and receive input; and
   a button for receiving input.

14. A wearable electronic device comprising:
   a housing comprising sidewalls for containing electronic components, an inner surface, an outer surface, and an opening;
   a cover member positioned over the opening; and
   a retention member configured to transition from a compressed configuration, in which the retention member is configured to pass through a portion of the cover member, to an expanded configuration, in which the retention member is configured to engage an inner portion of the cover member and the inner surface of the housing to secure the cover member against the outer surface of the housing.

15. The wearable electronic device of claim 14, wherein the retention member comprises:
a support section;
a flange extending radially outwardly from the support section to the inner surface of the housing; and
an engagement element extending radially outwardly from the support section to the cover member.

16. The wearable electronic device of claim 14, wherein further comprising a seal member between the housing and the cover member.

17. The wearable electronic device of claim 14, wherein the retention member has a first outer dimension while in the compressed configuration a second outer dimension while in the expanded configuration, the second outer dimension being greater than the first outer dimension.

18. The wearable electronic device of claim 14, wherein the cover member comprises:
a window;
an alignment element within an alignment channel of the housing; and
an engagement channel on a surface of the cover member.

19. The wearable electronic device of claim 18, wherein the window is a Fresnel lens that extends from an interior of the housing to an exterior of the housing.

20. The wearable electronic device of claim 18, wherein the window is aligned with a light source or a light detector.

* * * * *